United States Patent [19]
Frassica

[11] Patent Number: 5,871,475
[45] Date of Patent: *Feb. 16, 1999

[54] CATHETER SYSTEM

[76] Inventor: James J. Frassica, 5 Essex Pl., Chelmsford, Mass. 01824

[*] Notice: The term of this patent shall not extend beyond the expiration date of Pat. No. 5,601,537.

[21] Appl. No.: 585,040

[22] Filed: Jan. 11, 1996

Related U.S. Application Data

[63] Continuation-in-part of Ser. No. 436,194, Jun. 5, 1995, Pat. No. 5,601,537.

[51] Int. Cl.$^6$ .................................................. A61M 5/00
[52] U.S. Cl. ......................... 604/264; 604/95; 604/280; 604/349; 411/411
[58] Field of Search .............................. 604/50, 95, 280, 604/264, 349; 411/411

[56] References Cited

U.S. PATENT DOCUMENTS

| | | |
|---|---|---|
| 207,932 | 9/1878 | Alvord . |
| 761,235 | 5/1904 | Kepler . |
| 1,644,919 | 10/1927 | Hayes . |
| 1,888,349 | 11/1932 | Jacoby . |
| 2,173,527 | 9/1939 | Agayoff . |
| 2,896,629 | 7/1959 | Warr . |
| 3,428,046 | 2/1969 | Remer et al. ............................ 128/349 |
| 3,815,608 | 6/1974 | Spinosa et al. ......................... 128/349 |
| 4,445,509 | 5/1984 | Auth . |
| 4,762,130 | 8/1988 | Fogarty et al. . |
| 4,834,724 | 5/1989 | Geiss et al. . |
| 4,950,232 | 8/1990 | Ruzicka et al. . |
| 4,955,859 | 9/1990 | Zilber . |
| 5,009,643 | 4/1991 | Reich et al. . |
| 5,087,252 | 2/1992 | Denard . |
| 5,129,910 | 7/1992 | Phan et al. . |
| 5,246,445 | 9/1993 | Yachia et al. . |
| 5,308,354 | 5/1994 | Zacca et al. . |
| 5,313,934 | 5/1994 | Wiita et al. ............................... 128/4 |
| 5,334,211 | 8/1994 | Shiber . |
| 5,339,800 | 8/1994 | Wiita et al. ............................... 128/4 |

FOREIGN PATENT DOCUMENTS

| | | |
|---|---|---|
| 564832 | 1/1924 | France . |
| 9203077 | 7/1992 | Germany . |

OTHER PUBLICATIONS

"Anatomy, Descriptive & Surgical" by Henry Gray, 1977 Crown Publishers pp. 98–1001, 1004–1007, 1026–1027.

"Ancient Inventions", 1st Ed 1994 by Peter James & Nick Thorpe, Ballantine Books pp. 15 & 16.

"Perspective in Urology", Hoffman–Larducue, 1976 Pub of American Urological Assoc. pp. 117–134.

"Antique Medical Instruments", by C. Keith Wilbur, M.D., Schiffer Pub. Ltd., pp. 74–75.

"Urology Products", Bard Urological Div. 6 pages Product Data Sheets.

"A Presentation of Catheters and Urological Specialties for . . . " 1 page Foley Catheters/Urological Specialties.

*Primary Examiner*—Mark Bockelman
*Assistant Examiner*—N. Kent Gring
*Attorney, Agent, or Firm*—Vernon C. Maine; Scott J. Asmus

[57] ABSTRACT

Apparatus and methods using rotational advancement and emplacement of various devices for catheterization, dilation and occlusion of mammalian genito-urinary and gastro-intestinal passages and organs, where devices and assemblies have an external helical element present near the distal end which provides a longitudinal pull on the wall of the passage when rotational force is applied to the proximal end of the device.

12 Claims, 8 Drawing Sheets

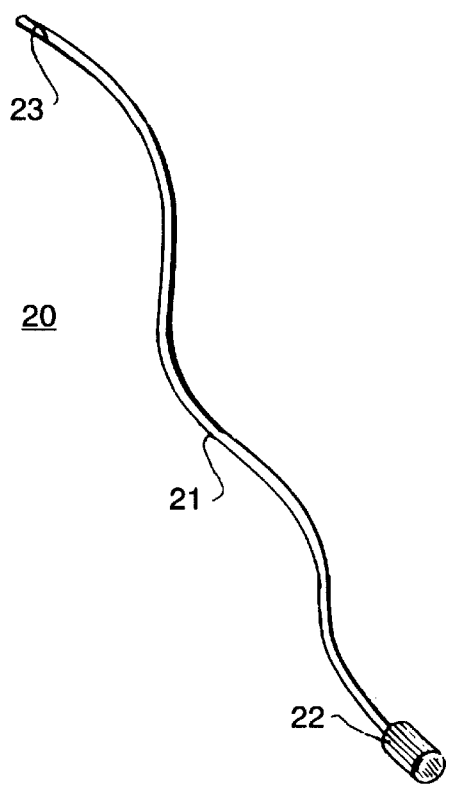
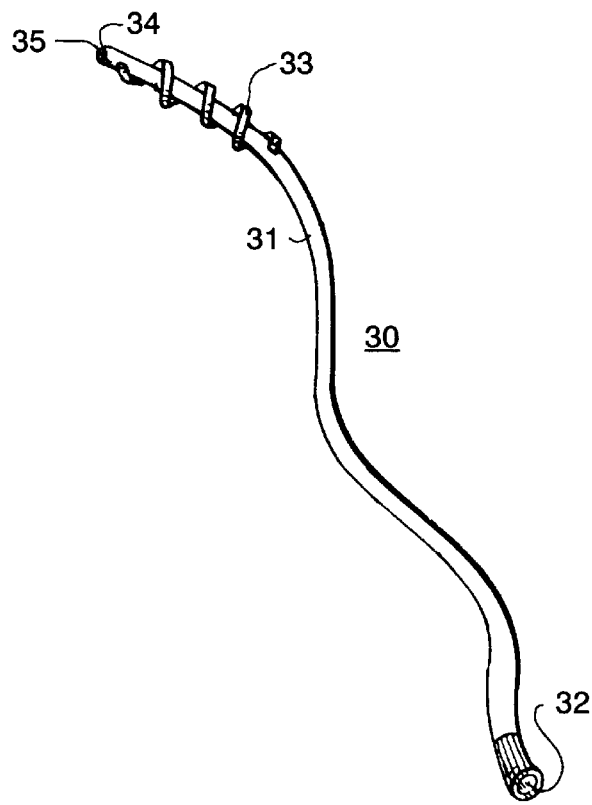
FIG. 4
FIG. 6
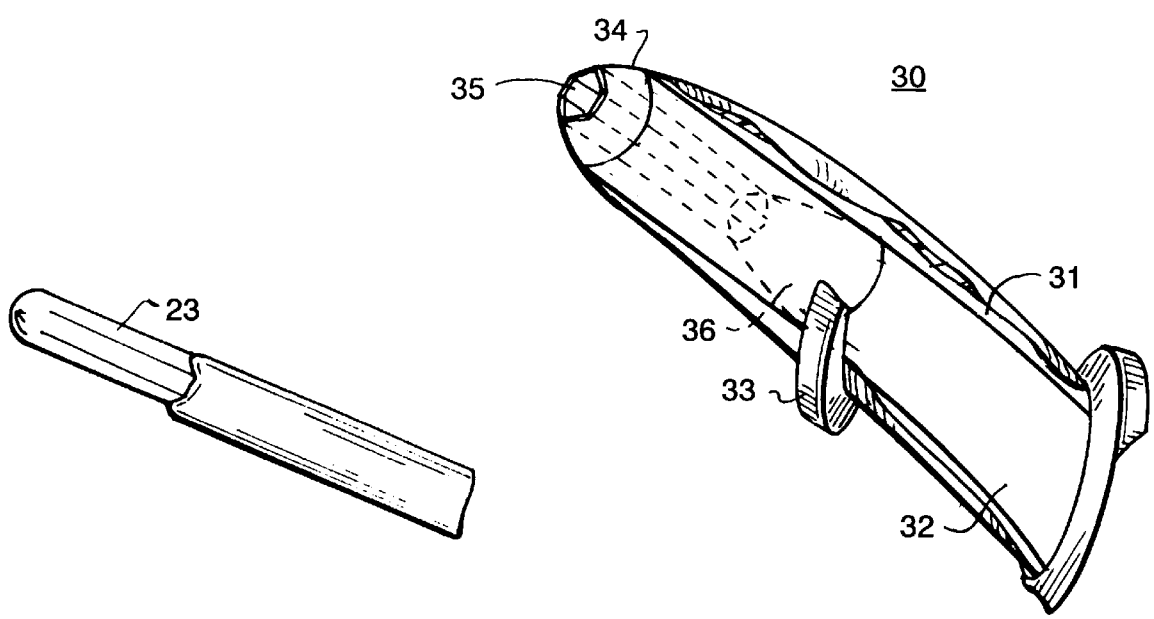
FIG. 5
FIG. 7

CATHETER SYSTEM

This application is a continuation-in-part to application Ser. No. 08/436,194, filed Jun. 5, 1995, by the inventor now U.S. Pat. No. 5,601,537.

BACKGROUND OF THE INVENTION

1. Technical Field of the Invention

This invention most generally relates to the apparatus and methods of catheterization and related treatments of the genito-urinary and gastro-intestinal passages of mammals.

More particularly, the invention relates to catheters, dilators, occluders and stents, and means of emplacement and application of the same to mammalian genito-urinary and gastro-intestinal passages.

2. Background Art

The background of this invention is bound up in the traditional "push to advance" methodology of catheter emplacement, which is characterized by external pressure on a stiff or thick-walled catheter to traverse a delicate, mucosal-lined passage. While the topic was extensively discussed in a prior pending application by this inventor, the following further remarks will provide additional context to aid in understanding the prior art and the problems associated with it, as well as the further disclosure and claims which follow.

As many men age, their prostates become enlarged and obstruct the flow of urine through the urethra. This condition is known as benign prostatic hyperplasia or BPH, and results in a partial or total inability to urinate. The most common surgical intervention for BPH, transurethral resection of the prostate, or TURP, has a lengthy recovery period of up to one year, and presents a high operative risk for complications such as sexual dysfunction. Up to 10% of those subjected to such surgery are left with mild to moderate stress incontinence.

Approximately 400,000 patients in the United States and approximately 500,000 patients internationally were diagnosed in 1994 with BPH or cancer-induced bladder outlet obstructions that were sufficiently severe to warrant TURP or alternative surgery, according to industry sources.

Because of the high costs, medical risks and quality of life compromises associated with TURP, new technologies have begun to challenge TURP's position as the standard treatment for severe BPH. Recently, the U.S. Food and Drug Administration approved two drugs, tera zosin hydrochloride and rinasteride, to treat BPH. These drugs generally do not improve symptoms for six to nine months after treatment begins, and are not without side effects.

Urethral strictures are often due to fibrous tissue growth resulting from reaction to catheters or cystoscopes or from injury, birth defects or disease, and are commonly treated by urethral dilation, catheterization or surgery. Men with urethral strictures also experience a limited ability to urinate, which may cause extreme discomfort and, if left untreated may cause complications that necessitate catheterization.

The standard catheterization means for hospitalized and bed ridden patients is the Foley Catheter. The Foley or indwelling urethral catheter is pushed into the bladder and retained by a water-filled balloon at the distal end. It drains urine continuously from the bladder via a connecting tube into a bag worn on the leg or hung on the bed. But difficulty in placement has always been inherent in this design. This is due to the traditional "push to advance" technology, which necessitates a stiff thick-walled catheter to traverse the delicate mucosal lined urethra.

Often the French (unit of measurement) size of the catheter is dictated by the need for stiffness to insert rather than the lumen size to pass urine. A 14 French or smaller Foley is rarely used because catheters of this size lack the column strength needed to push the full length of the urethra into the bladder. The larger French Foley catheters are painful to place, uncomfortable when indwelling, and require a highly skilled care provider to insert.

Dilation is accomplished by pushing successively larger urethral dilation tubes through the urethra to increase the size of the lumen, a procedure which is painful and traumatic to the patient. Of course, any catheterization of a restricted passageway is inherently a dilation process. Surgical treatment of strictures involves surgical risks as well as complications, including infection, bleeding and restenosis, which requires further treatment.

Approximately 50,000 patients in the United States were diagnosed with recurrent urethral strictures in 1994, according to industry sources. The inventor estimates that approximately 75,000 additional patients were diagnosed internationally.

Women suffer from urinary incontinence far more often than men and at an younger age primarily because of the stress associated with pregnancy and childbirth, the shorter length of the female urethra, and the absence of a prostate. The U.S. Department of Health and Human Services (HHS) estimates that the involuntary loss of urine affects approximately 10 million Americans of which 8.5 million are women. Seven million of these women are non-institutionalized, or community-dwelling.

For women between the ages of 15 and 64, the prevalence of urinary incontinence is estimated to range from 10 to 25 percent of the population. For non-institutionalized persons over the age of 60, the prevalence of urinary incontinence ranges from 15 to 30 percent, with the prevalence in women twice that of men.

The involuntary loss of urine can be caused by a variety of anatomical and physiological factors. The type and cause of urinary incontinence is important to how the condition is treated and managed. The two broad categories of urinary incontinence are urge and stress incontinence. Some people suffer from what is termed mixed incontinence or a combination of stress and urge incontinence Urge incontinence is the involuntary loss of urine associated with an abrupt and strong desire to void. In most cases, urge incontinence is caused by involuntary detrusor (the smooth muscle in the wall of the bladder) contractions or over-activity. For many people, urge incontinence can be satisfactorily managed with pharmaceuticals.

The more frequently occurring stress incontinence is the involuntary loss of urine caused by movement or activity that increases abdominal pressure. The most common cause of stress incontinence is hypermobility or significant displacement of the urethra and bladder neck during exertion. A less frequent cause of stress incontinence is intrinsic urethral sphincter deficiency (ISD), a condition in which the sphincter is unable to generate enough resistance to retain urine in the bladder. Medical professionals have categorized stress incontinence into three types. They are:

Type I—slight amount of hypermobility. This is a mild form of incontinence: about 25% of stress incontinence are in the group.

Type II—A severe condition of hypermobility that characterizes an estimated 60% of stress incontinence sufferers.

Type III—Caused by ISD and often so severe that a patient will leak while standing still. This group constitutes about 15% of the stress incontinence population.

Occluders are used in some cases to control incontinence. Occluders of the prior art are constructed and applied with the same push-to-advance concept as catheters and dilators described above, with the same liabilities. The basic occluder is a bulb or plug on a shaft which is inserted within a passageway to stop or prevent the normal flow of materials through the passageway, or driven all the way into the bladder, for example, and allowed to seat as a plug at the neck of the urethra to prevent the flow of urine from the bladder.

Intermittent catheterization is mainly used by people who are incontinent due to a failure of the nerves that link the bladder and the brain. This is called neuropathic bladder, and may occur in a wide variety conditions which include spina bifida, multiple sclerosis, spinal injury, slipped disc and diabetes. Intermittent catheterization may also be utilized by people who cannot empty the bladder because the bladder muscle is weak and does not contract properly.

Conventional intermittent catheters are simple tubes with a drain port at the internal end that enters the bladder. These tubes are usually smaller in diameter and stiffer than an indwelling catheter of the same size. This stiffness can make traditional push-to-advance catheterization difficult in men because the urethra is long and has an acute bend within the prostate. When the external sphincter is reached with a conventional catheter the sphincter muscle will contract making passage difficult.

Dilators, occluders and catheters of the prior art share the 4000 year-old push-to-advance technology where an ever present problem exists in making them stiff enough for full penetration of the subject passage and yet flexible enough to make the turns without undue risk of trauma, pain or puncture to the wall of the passageway when being pushed in. Self-administration is inhibited by all of the shortcomings of the present art, and further injury, infection and discomfort may result from the resulting improper self-care.

In some patients, an alternate apparatus and method used to maintain long term drainage of the bladder is the use of a suprapubic tube.

Suprapubic catheterization of the bladder is performed via transabdominal puncture which enters the body above the pubic arch and is directed into the bladder using ultrasound or fluoroscopy to guide the trocar introducer and suprapubic catheter. The needle introducer is then removed when proper catheter placement within the bladder is confirmed, leaving the drainage catheter in place.

Long term drainage may require the fixation of the catheter at the skin using standard adhesive based interface components to address mechanical fixation, inflection control, and skin compatibility.

The distal end of the catheter is commonly contained within the bladder by inflated balloon, winged-shaped tip configurations which expand within the bladder, or pre-shaped curved catheter tips which curl to their original J-shape when stiffening wire is removed from the catheter lumen.

A problem with this form of distal end emplacement is that it is only unidirectional; that is, it only resists the inadvertent pulling out of the tip of the catheter from the wall of the bladder, while allowing the catheter to freely pass further into the bladder, and back out up to the point of the containment structure. This continuing catheter motion in and out of the bladder may irritate tissue and cause infection or other difficulty at the bladder-catheter interface. Urine is especially irritating to most parts of the human body that are outside the urinary tract.

SUMMARY OF THE INVENTION

For the purposes of this disclosure, including the appended claims, the terms "distal", "distally", and "distal end", as they relate to the devices and methods described herein, refer to the end of the device further from or in the direction away from a practitioner who might be applying the device or method to the subject. Stated conversely, the terms refer to the end of the device closer to or in the direction towards the subject's interior; or in plain language, the front end of the device or direction in which the device is moved to be advanced into the subject's body.

The terms "proximal", "proximally", and "proximal end", as they relate to the devices and methods described herein, refer to the end of the device closer to or in the direction towards the practitioner who might be applying the device or method. Stated conversely, these terms refer to the end of the device further from or in the direction away from the subject's interior; or in plain language, the back end or external end or direction in which the device is moved to be retracted out of the subject's body.

These definitions simply restate the common usage of the terms as applied to the subject matter of this disclosure, as will be appreciated by practitioners in the art.

Objects of the invention include providing and employing screw-based means for rotational advancement and anchoring of catheters, occluders, stents, and dilators into genito-urinary and gastro-intestinal passageways such as the urethra, ureter, esophagus and fallopian tube, and for the emplacement of suprapubic catheters for draining genito-urinary organs such as the bladder, whereby the subject device is drawn through the passage by the longitudinal pull of a helix on the walls of the passage or organ as the distal end of the device is rotated. This technology is a radical departure from the 4000 year old traditional "push to advance" methodology previously discussed.

As has been disclosed and claimed by this applicant in the parent application, now U.S. Pat. No. 5,601,537, rotational advancement of catheters and like apparatus in genito-urinary and gastro-intestinal passages can be accomplished with substantially no pushing effort when the distal end of the apparatus is configured with an external screw thread of uniform pitch, the thread having a thread height of at least one fifth (⅕) of the outside diameter of the apparatus and a thread pitch not greater than the circumference of the thread. The screw-based means of the parent application is herein extended to the several devices, methods and applications disclosed. Accordingly, the ratio of the dimensions of the devices disclosed and claimed herein should be read to conform to this limitation.

Flexible, thin wall indwelling and intermittent catheters and related devices and delivery stylets, made possible by this form of emplacement, are less traumatic and easier for the medical practitioner or patient to use. Once placed, the device is anchored by the radial force and friction of the helix, preventing longitudinal migration due to body movement or fluid flow. This technology fosters reduced costs for patent care, improved clinical outcomes and enhanced patient quality of life.

The prostate stent of the invention, indicated for bladder outlet obstructions, is intended for BPH patients who are not able to, or choose no to undergo TURP. The prostate stent keeps the urethra open in the area of the prostate. The stent body may be between 3.5 cm and 6.5 cm in length depending on the anatomy, and has a helical element on the outer diameter of the body to advance and retain the stent. The sidewall of the stent may have a reinforcement means to prevent collapsing due to prostate pressure. The stent can be inserted in the urethra under fluoroscopy, using a detachable flexible stylet which keys into the proximal end of the stent body, and may be inserted in an outpatient procedure using topical anesthesia.

The urethral stent of the invention may be implanted in the male urethra as an alternative to dilation, catheterization and surgery. It keeps the urethra open by providing support under the stricture, thereby permitting passage of urine. The stent body may be between 3.5 cm and 6.5 cm in length depending on the anatomy, and has a tapered helix on the outer diameter of the body to advance and retain the stent. The sidewall of the stent may be reinforced to prevent collapsing due to prostate pressure.

The prostate and urethral stents of the invention may be inserted in the urethra using a detachable flexible stylet which keys into the proximal end of the stent body, and may be inserted in an outpatient procedure using topical anesthesia. The stent is not susceptible to being incorporated by the urethral mucosa in a manner preventing rotation, thereby permitting a lengthy period of emplacement and subsequent removal by the same rotational technique. The stent may also have a sufficiently large internal diameter, or lumen, to permit cystoscopies, thereby allowing examination of the bladder without removing the stent.

The male continence catheter of the invention, indicated for bladder outlet obstructions, is intended for BPH patients who are not able to, or choose not to undergo TURP. This embodiment of the invention allows the urethra in the area of the prostate to remain open. The catheter is inserted in the urethra by the user on a daily basis and taken out prior to sleeping. This catheter offers an effective option to surgery. It gives the patient the ability to regain control with a disposable catheter that is easily inserted into the urethra and worn during the day, and then removed and disposed of before retiring for the night.

The methodology of this catheter uses the core helix technology to enable easy insertion and retaining of the device. The catheter shaft may have a short tapered semi-pneumatic helix on the distal 2 cm (bladder end) of the shaft, and a drainage port at the distal end of the shaft. At the proximal (external end) there may be a flow valve which can be depressed to empty the bladder. It may be produced as a sterile, single-use, disposable item that can be used intermittently when the patient desires.

The patient simply inserts the catheter into the urethral opening and rotates the shaft to advance the catheter into the bladder. This can be done in the morning in the convenience of home. When the user needs to urinate, the valve end of the flexible shaft may be exposed through the clothing and the valve opened to empty the bladder. Since the device is not removed and reinserted after each voiding the risk of infection is reduced. At the end of the day the catheter is easily removed and disposed.

Another embodiment of the catheter of the invention provides a female Stress UI sufferer with lifestyle benefits that greatly outperform absorbent products intended to manage this condition. The catheter uses the core helix technology to enable easy insertion and retaining of the device. The catheter shaft may have a short tapered semi-pneumatic helix on the distal 2 cm (bladder end) of the shaft, and a drainage port at the distal end of the shaft There may be a flange 3.5 cm from the distal end which seats in the urethral opening to position the catheter. At the distal (external end) there may be a flow valve which is opened to empty the bladder. It may be supplied as a sterile, single-use, disposable item that can be used intermittently when the patient desires.

The female patient simply inserts the catheter into the urethral opening and rotates the shaft to advance the catheter into the bladder. This can be done in the morning in the convenience of the patient's own home. There are no applicators to attach or dispose of. When the user needs to urinate, the valve end of the flexible shaft is extended through the clothing or otherwise exposed, and the valve is opened to empty the bladder.

Since the device is not removed and reinserted into the urethra after each voiding the risk of infection is greatly reduced. Another benefit of this system is the user can void while standing, which may be of concern when using unsanitary public restrooms. At the end of the day the catheter is easily removed and disposed of.

The invention eliminates the push-to-advance characteristic of the traditional Foley Catheter by utilizing rotational advancement so that the catheter is drawn through the urethra by the longitudinal pull of the helix on the walls of the passage as the distal end of the device is rotated.

In this embodiment, the helix is located on the shaft under the balloon and disappears when the balloon is inflated. The flexible reinforced shaft need be only about half the wall thickness of conventional Foley Catheters, which means a smaller OD catheter can be used. The helix advances the shaft and dilates the urethra as the catheter is inserted. Once the bladder is reached the balloon is inflated with sterile water and the helix is engulfed by the balloon. The process is then reversed to remove the catheter.

Helically-adapted dilators and occluders of the invention are likewise rotatingly advanced and retracted; the helical element performing a dilatory function to some degree. Dilators of respectively larger diameters may be used to achieve a gradually more pronounced effect.

The rotational advancement means may be combined with the push-to-advance methodology in any of these devices. In a dilator, for example, a helically equipped leader shaft extending distally of the bulbous portion of the device rotatingly advances the device up to the point that the helix passes out of the interior end of the passage, the remainder of the leader shaft then providing a guide wire that leads the bulb through the remainder of the passageway when the dilator is pushed from the proximal end.

The adaptation of the invention to suprapubic catheters used in a classic transabdominal puncture for the drainage of the bladder or other genito-urinary organs, permits the helix on the distal end of the catheter to be emplaced in the wall of the organ far enough so that the helical vane extends from both sides of the organ wall, so that the longitudinal sliding motion of the catheter into and out of the organ is inhibited by the helical vane. This reduces a source of irritation and associated complications at the organ wall entry point.

The helically-adapted suprapubic catheter may be placed in the organ using ultrasound or fluoroscopy to visualize placement, by rotatingly advancing the catheter over a guidewire leading to the organ; the guidewire having been installed through a tubular access created by using a cannula and trocar to reach the organ, the trocar and the cannula having been successively removed.

Any embodiment of the invention may be radiopaque, or have radiopaque features, markers or other components, permitting the use of fluoroscopy to monitor emplacement or removal of the device, or even the rotational orientation and rotational movement.

Embodiments or elements of the invention may be fabricated, molded, wound, extruded or otherwise constructed of non-toxic, non-corrosive materials or combinations of materials that are otherwise tolerant of bodily fluids and durable when implanted in vivo. Such materials may include but are not limited to polyurethane, medical grade stainless steel, silicone, bicarbon, polytetrafluoroethylene, tantalum, titanium, or nickel-titanium alloy. Conversely, materials may be specifically chosen to be bioabsorable so as to obviate the need for removal.

A variation of the catheter of the invention eliminates the problems of conventional intermittent catheterization by using helix or rotational technology that provides controlled insertion and flexibility to negotiate the urethra. The helix design accomplishes a pre-dilatation of the passageway at a steady rate that relaxes the sphincter and lessens or prevents spasm.

The catheter shaft has a short tapered helix on the distal 2 cm (bladder end) of the shaft, and a drainage port at the distal end of the shaft. It is designed as a sterile, single-use, disposable item that can be used when the patient believes it is appropriate. The patient simply inserts the sterile catheter into the urethral opening and rotates the shaft to advance the catheter into the bladder. When the urine stops flowing the catheter is easily removed and disposed.

BRIEF DESCRIPTION OF THE DRAWINGS

FIG. 4 is a perspective view of a stylet with a grip on it's proximal end and a hexagon drive tip on it's distal end.

FIG. 5 is a perspective view of the hexagon drive tip of the stylet of FIG. 4.

FIG. 6 is a perspective view of a stent-follower with a helical element at it's distal end.

FIG. 7 is a cross section closeup view of the distal end of the stent-follower of FIG. 6, showing the hidden portion of the bushing with it's hexagonal drive aperture in dashed lines.

DESCRIPTION OF THE PREFERRED EMBODIMENT

Figure 1:
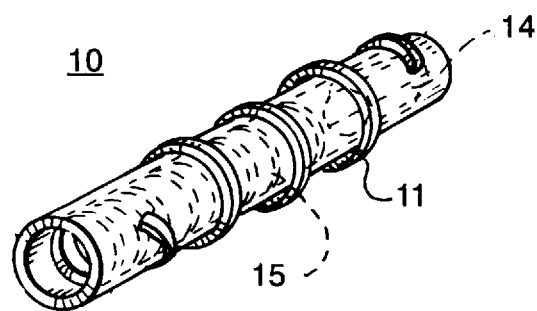
FIG. 1 is a perspective view of a stent with an external helical element, dashed lines showing an internal sidewall reinforcement member and a bushing with a hexagon drive socket.

To those skilled in the art, the invention admits of many variations and appellations in apparatus and methodology.

By way of example, there is provided in accordance with the present invention, a screw-based means for advancing a catheter, dilator or occluder into mammalian genito-urinary or gastro-intestinal passages such as the urethra or ureter, for the usual purposes associated with such devices where no incising or rupture of passage walls or membranes is intended. Placement may be for a few minutes up to several weeks, or longer, depending on the condition and the requirements of the patient.

As another example, a stent may be adapted to have an externally applied helical element in the form of a raised thread of one or more turns of uniform pitch, and be configured to be rotatingly advanced into such a passage by use of a stylet. The stylet may be axially engaged into the proximal end of the stent in a non-rotational manner. Rotational force applied to the proximal end of the stylet is transmitted by the shaft to the stent and hence to the helical element, which by turning produces a longitudinal pull on the wall of the passageway, advancing the stent and the stylet.

As yet another example, the stent may be used with a follower device, a tube with a helical element near it's distal end, and a lumen of sufficient size to pass the stylet through, where the distal end of the lumen is equipped with a non rotational fitment that can be interlocked by the stylet or other means with the stent, so that the follower, stylet and stent must all be rotated together. When the stent is in place, the stylet can be withdrawn and the follower rotatingly withdrawn.

As still yet another example, the stent may incorporate a means for manual, automatic, or periodic flow control.

As even still yet another example, the invention may be applied to a Foley-type catheter for genito-urinary and gastro-intestinal passages, where the flexible tube of the catheter has a main lumen extending from the drainage port at the distal end to the proximal end of the tube for drainage. An external helical element in the form of a raised thread of uniform pitch is applied near the distal end, with a thin-walled inflatable balloon encompassing the helical element so tightly that the helical element is still functional for rotational advancement of the catheter.

The balloon terminates on the tube above and below the helical element. An inflation lumen extends from an inflation port on the tube within the balloon, to the proximal end of the tube. After the catheter is advanced through the passage with the helical element in the body chamber beyond, fluid is introduced through the inflation lumen to inflate the balloon, thus locking the catheter in place.

As an additional example, a dilator in accordance with the invention, for use in genito-urinary and gastro-intestinal passages, has a flexible shaft incorporating a tapered bulb, with a least one helical element or external thread segment disposed on it, and is administered by the methods of the invention.

As another additional example, an occluder for genito-urinary and gastro-intestinal passages is constructed similarly to a dilator of the invention, except that there is no helical element at the midpoint, or point of largest diameter of the bulb, so that the blocking or plug function of the occluder is uniformly applied to the walls of the passage.

As still another additional example, an occluder may have one helical element disposed above the midpoint of the bulb and another helical element disposed on the flexible shaft below the bulb, to facilitate advancing and retracting the occluder through a passageway into a body cavity into a cavity for occluding the interior entrance to the passage.

As yet still another additional example, a dilator of the invention may utilize a combination of rotating advancement means and push-to-advance means, where a helical element is configured on the distal end of a shaft or tube, followed by a dilator sleeve further aft or proximally of the helix. The shaft or tube is rotatingly advanced until the helix passes through and out of the interior end of the passage, leaving the dilator sleeve somewhere within the passage with the shaft or tube extending distally of the dilator sleeve providing a physical guide shaft through the remainder of the passage, so that the dilator can then be pushed from the proximal end to advance the dilator sleeve through the remainder of the passage.

As a further example, occluders of the invention, with tapered bulbs incorporated near the distal end of a shaft or tube, are adapted for rotational advancement with helical elements disposed at least near their distal ends. A smooth mid section or proximal end section of the tapered bulb provides the occluding structure of the device.

As another further example, a suprapubic catheter for draining genito-urinary organs such as the bladder may adapted with the helical element for rotating advancement in accordance the invention along a guidewire through the abdomen, and subsequent emplacement in the wall of the organ. The exterior or proximal end of the catheter being affixed in a non-rotational manner to the abdomen wall, typically by adhesive means, the helical element or vane then prevents lengthwise or longitudinal movement of the catheter that might otherwise cause irritation, leakage or even dislodge the distal end from the organ. The guidewire may be installed by any conventional or novel means, including the use of a trocar and cannula.

As still another further example, any device of the invention, including the suprapubic catheter, may be configured with radiopaque or other externally detectable markers or means for determining the rotational position or orientation, and any rotational movement of the distal end of the device during or after emplacement.

Figure 2:
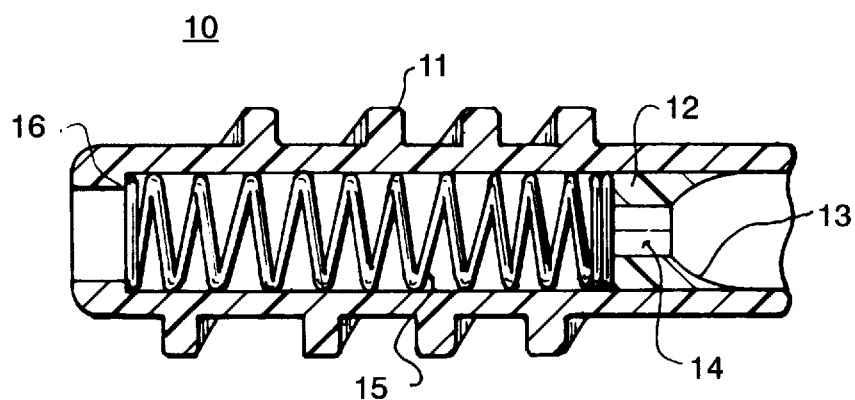
FIG. 2 is a cross section view of the stent of FIG. 1.
Figure 3:
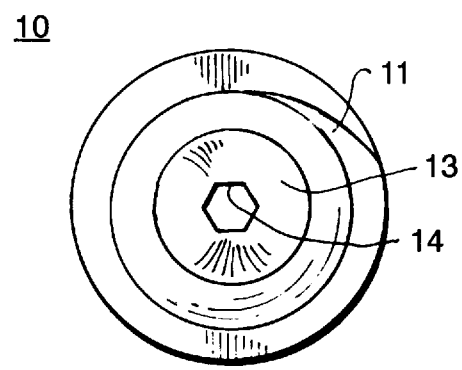
FIG. 3 is a proximal end view of the stent of FIG. 1, with the hexagon drive socket visible at the center.

Referring now to FIGS. 1–3, a urethral stent 10 made from polyurethane material has a helical element 11 applied to it's external surface in the form of a raised thread of uniform pitch. The ends of helical element 11 are tapered for ease of advancing and retracting. There is an interior shoulder 16 at the distal end of stent 10, and a bushing 12 of relatively harder material with a tapered interior wall 13 extending from the bushing's full diameter at one end to a uniform hexagonal aperture 14, bushing 12 being affixed within the distal end of stent 10 and oriented with tapered wall 13 extending distally from aperture 14. Coiled sidewall reinforcement member 15 is secured within the remaining length of stent 10 by sleeve 12 and interior shoulder 16.

Referring now to FIGS. 4 and 5, stylet 20 has flexible shaft 21 with grip 22 at the proximal end for turning, and hardened hexagon tip 23 at the distal end, which closely fits into aperture 14 of stent 10 in a non-rotational manner for emplacement of the stent by the method of the invention. The flexible shaft 21 of stylet 20 is sufficiently strong such that when tip 23 is inserted into aperture 14, the shaft will withstand and transmit torque as applied by rotational finger force at grip 22 to the helical element 11 of stent 10.

Referring now to FIGS. 6 and 7, stent-follower 30 has a flexible tube 31, lumen 32 of which is sized to accept the ready insertion of tip 23 and shaft 21 of stylet 20. Tube 31 is of sufficient torsional strength to accept and transmit rotational finger force at it's proximal end to it's distal end. A helical element 33 is applied to external surface of tube 31 near it's distal end, in the form of a raised thread of uniform pitch. The ends of helical element 33 are tapered for ease of advancing and retracting.

Bushing 34 has a uniform hexagonal aperture 35 the same size as aperture 14 of stent 10, and a tapered interior wall 36 extended from it's full diameter at it's proximal end to aperture 35. Bushing 34 also has a tapered tip at it's distal end. Bushing 34 is affixed within the distal end of tube 31 with the tapered tip protruding, such that the distal end of stent-follower 30 mates with a self-centering action with the proximal end of stent 10 when the two are brought into contact with approximate axial alignment. When stent-follower 30 and stent 10 are thus mated, tip 24 of stylet 20 may be extended through aperture 35 and into aperture 14, thereby locking stent 10 and stent-follower 30 into a fixed rotational relationship. In this condition, the rotation of the proximal end of stylet 20 and stent-follower 30, causes the concurrent rotation of stent 30.

Figure 8:
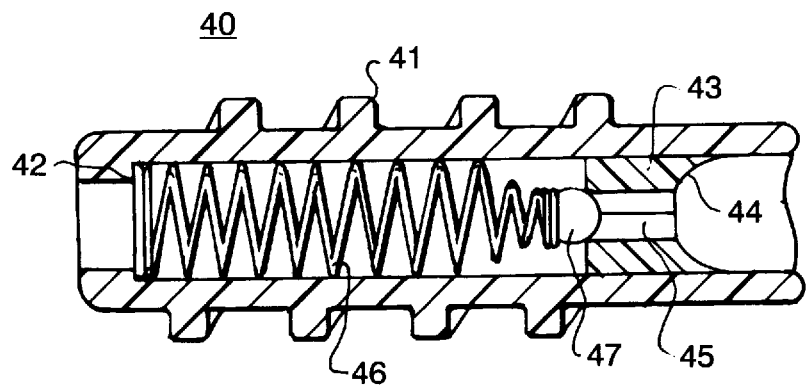
FIG. 8 is a cross section view of a stent with flow control, showing the coiled wall reinforcement member acting as a spring on the ball of the check valve.

Referring now to FIG. 8, stent 40, shown in cross section, is made from a section of extruded polyurethane tubing material, and has a helical element 41 applied to it's external surface in the form of a raised thread of uniform pitch. There is an interior shoulder 42 at the distal end of stent 40, a bushing 43 of relatively harder material with a tapered interior wall 44 extending from the bushing's full diameter at one end to a uniform hexagonal aperture 45, bushing 43 being affixed within the distal end of stent 40 and oriented with tapered wall 44 extending proximally.

A coiled sidewall reinforcement member 46 and a check ball 47 are secured within the remaining length of stent 40 by bushing 43 and interior shoulder 16 so that coiled member 46 holds ball 47 in compression against the upper end of bushing 43 in the manner of a check valve which prevents flow through the lumen of stent 40. Coiled member 46 may be compressed by upward movement of ball 47, thereby opening the check valve to flow.

Figure 9:
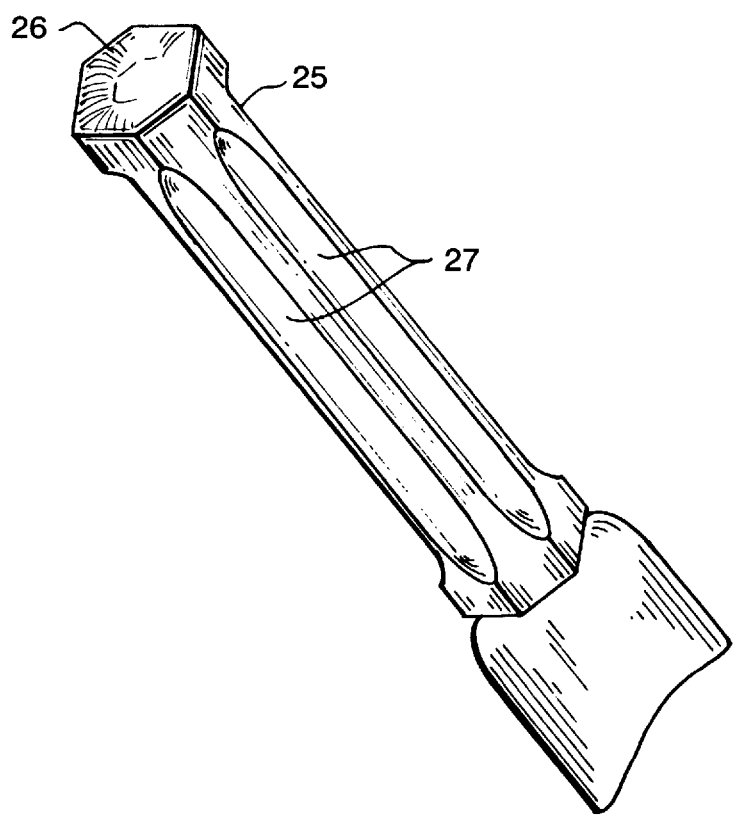
FIG. 9 is a closeup perspective view of a special stylet tip for operating the check valve of the occluder of FIG. 8.

Referring to FIG. 9, alternate tip 25 for stylet 20 has a slightly concave proximal end 26 and flutes 27. When used in conjunction with stent-follower 30, tip 25 may be inserted through aperture 45 of stent 40 and used to push ball 47 upward against coil member 46, permitting flow through flutes 27 and aperture 45.

Figure 10:
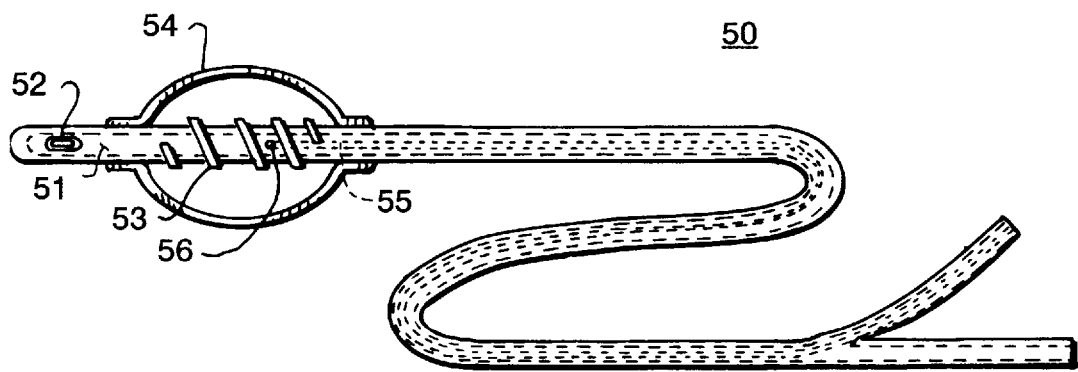
FIG. 10 is a diagrammatic longitudinal cross section view of a balloon catheter showing the helical element inside the inflated balloon, with lumens shown as dashed lines.
Figure 11:
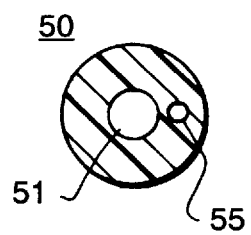
FIG. 11 is a cross section view of the shaft of the catheter of FIG. 10, showing the central drain lumen and the smaller inflation lumen.
Figure 12:
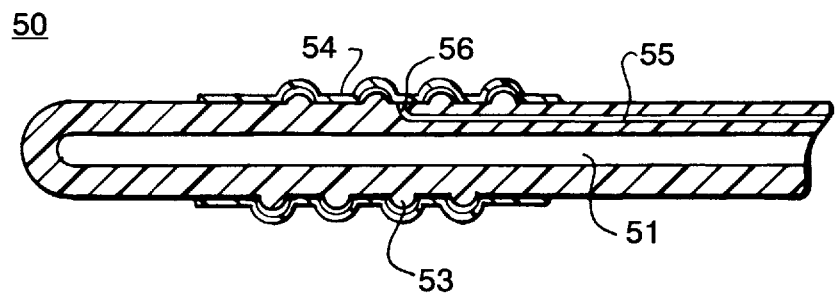
FIG. 12 is a longitudinal cross section view of the distal end of the catheter of FIG. 10, showing the balloon contracted around the helical element.

Referring to FIGS. 10, 11 and 12, a catheter 50 of the invention is made from polyurethane material. It has an axial drain lumen 51 running from a drain port 52 at it's distal end to it's proximal end, and a helical element 53 applied to it's external surface near it's distal end in the manner of a raised thread with a uniform pitch. The ends of helical element 53 are tapered for ease of advancing and retracting. Catheter 50 has a thin-walled inflatable balloon 54 encasing the helical element 53, and a smaller inflation lumen 55 in the sidewall running from inflation port 56 within the envelope of balloon 54 to the proximal end of catheter 50.

Balloon 54, when uninflated, is normally contracted tightly about helical element 53 as illustrated in FIG. 12, and may be inflated as in FIG. 10 by injecting fluid into the distal end of lumen 55. The flexible shaft of catheter 50 is of sufficient torsional strength to withstand and transmit rotational finger force at the distal end to helical element 53.

Figure 13:
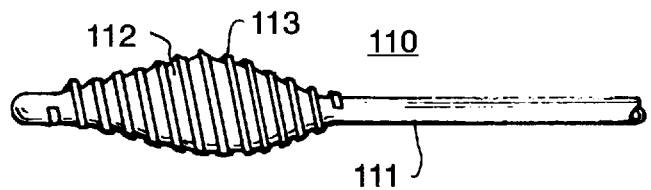
FIG. 13 is a side elevation of a helically adapted dilator.
Figure 14:
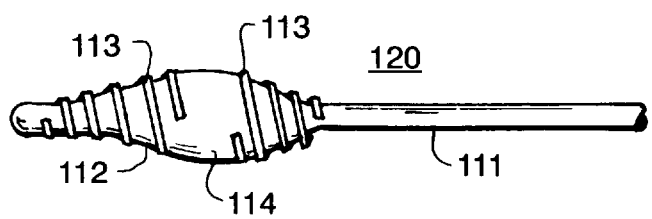
FIG. 14 is a side elevation of a helically adapted occluder.
Figure 15:
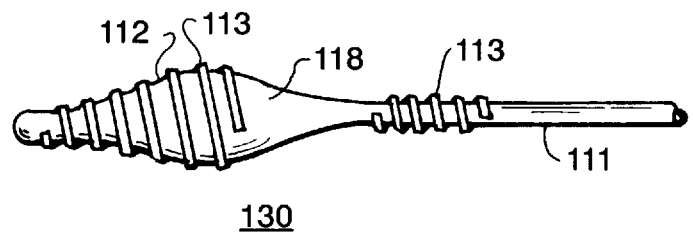
FIG. 15 is a side elevation of another helically adapted occluder.

Referring now to FIGS. 13–15, dilator 110, occluder 120, and occluder 130 are similarly constructed of polyurethane and used in accordance with the invention by configuring the distal end of a flexible shaft 111 with tapered bulb 112, and disposing thereon helical elements 113 in the form of raised threads of uniform pitch in locations as shown in the figures. Shaft 111 is of sufficient torsional strength to accept and transmit rotational finger force at it's proximal end to it's distal end. The ends of helical elements 113 are tapered for ease of advancing and retracting the devices in a passageway.

Dilator 110 has a helical element 113 disposed over the full length of bulb 112. Occluder 120 is distinguished from dilator 110 in that there is no helical element present at the center section 114 where the diameter of tapered bulb 112 is greatest, thus providing occlusion within a passageway.

Occluder 130 is distinguished from dilator 110 and occluder 120 by having no helical element present on the lower section 118 of bulb 114, but rather a smooth circular surface with which to occlude a passageway at it's interior entrance. One helical element 113 is present lower on shaft 112, which would remain within the subject passage and retain a longitudinal grip on the passageway wall when the upper helical element 113 passes into a cavity and loses it's grip.

Figure 16:
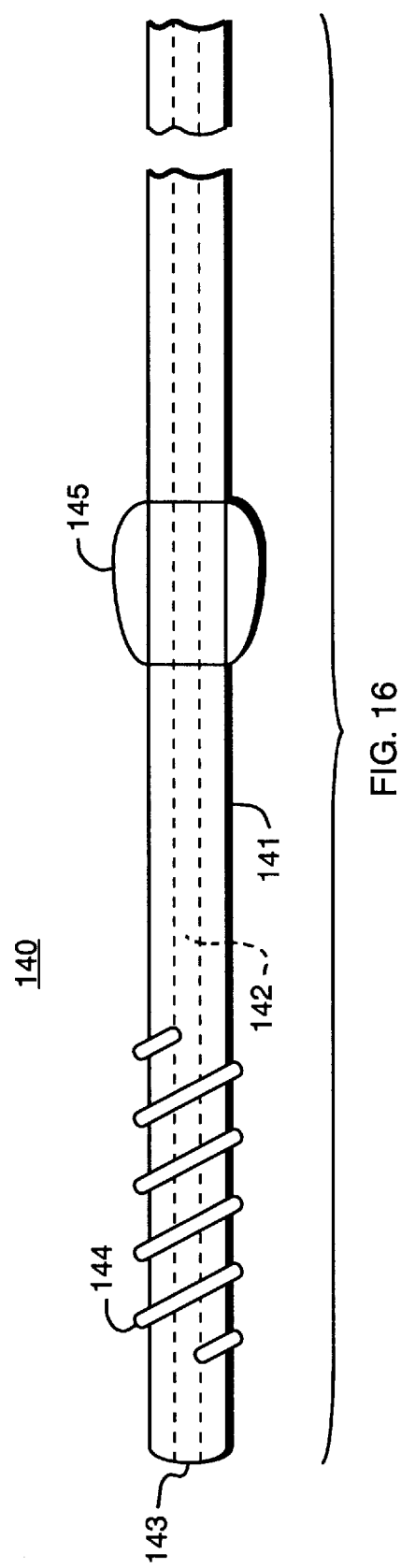
FIG. 16 is diagrammatic side view of a dilating catheter.

Referring now to FIG. 16, dilator 140 has a flexible shaft 141 with a lumen 142 connecting drainage port 143 at it's distal end to it's proximal end, an external helical element 144 applied to the external surface near the distal end in the form of a raised thread of uniform pitch, and external dilating sleeve 145 with tapered ends affixed below or behind helical element 144. Shaft 141 is of sufficient torsional strength to accept and transmit rotational finger force at the distal end to the distal end. The ends of helical element 144 are tapered for ease of advancing and retracting the device in a passageway.

A method of the invention for dilation uses a series of catheter 140's in graduated sizes. The distal end of a smaller size catheter 140 is inserted into the subject passageway sufficiently far to engage the helical element 144. The catheter is rotatingly advanced by rotating the shaft 141, resulting in dilating sleeve 145 being pulled through the passageway until helical element 144 passes through and out of the other end of the passageway.

With the distal end of shaft 141 now extending from dilating sleeve 145 on through the passageway acting as a guide, the shaft may be pushed from the proximal end to advance the dilating sleeve the remaining short distance through the passageway.

The catheter may then be withdrawn until the helical element 144 is re-engaged with the passageway, and rotatingly withdrawn through the passageway. The method may be repeated with respectively larger dilator 140s until the desired amount of dilation is achieved.

Figure 17:
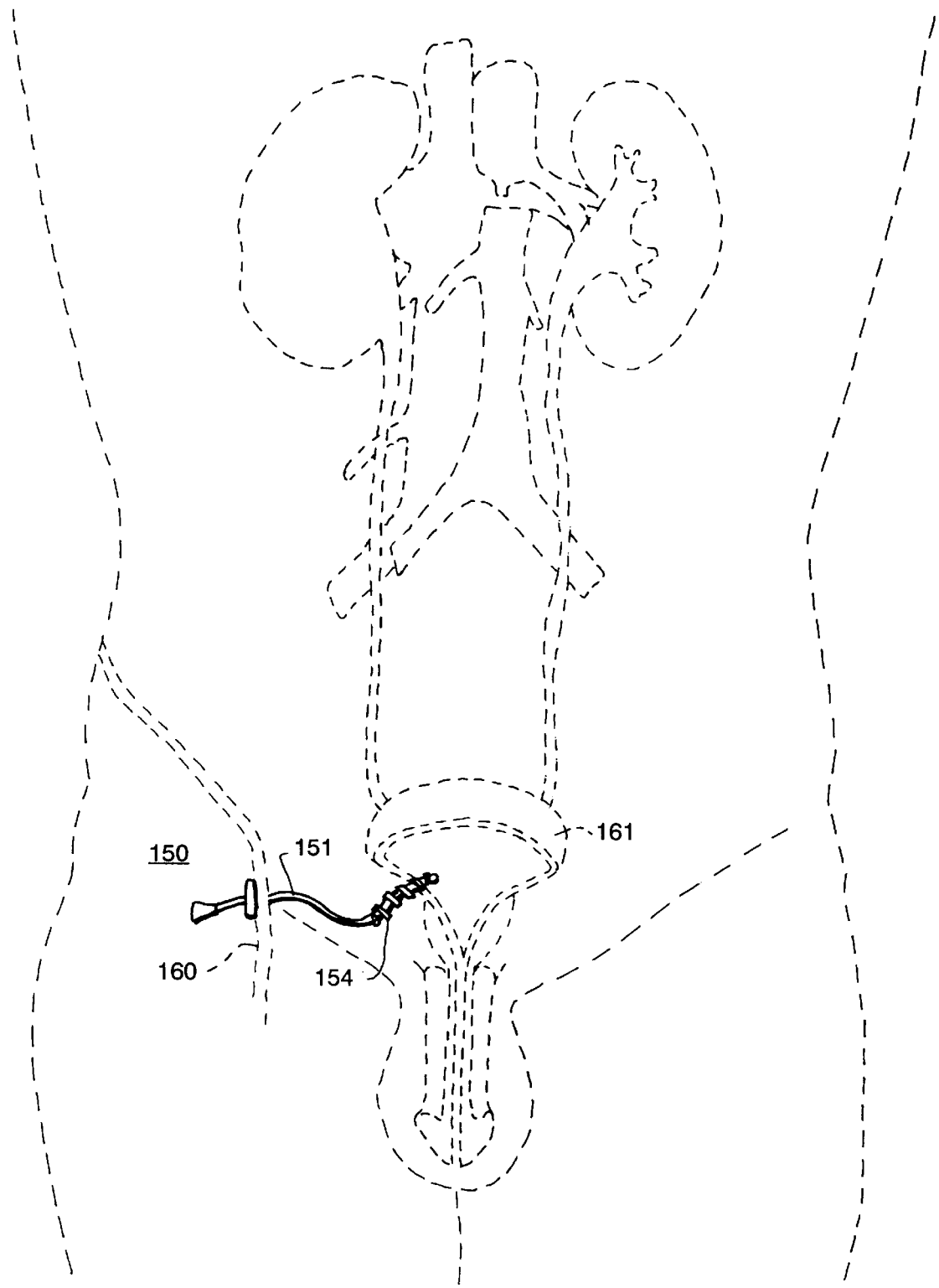
FIG. 17 is a diagrammatic illustration of a suprapubic catheter emplaced in the abdomen with the distal end locked by it's helical element in the bladder wall.
Figure 18:
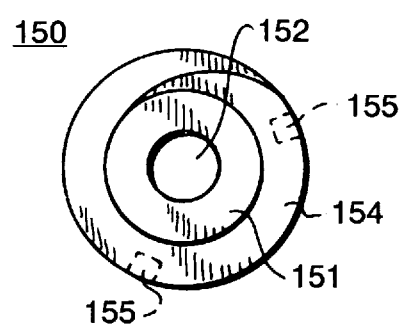
FIG. 18 is a distal end view of the suprapubic catheter of FIG. 17, showing rotational orientation markers.

Referring now to FIGS. 17–18, a suprapubic catheter 150 has a flexible shaft 151 with a lumen 152 connecting the proximal end to the distal end, an external helical element 154 applied to the external surface near the distal end in the form of a raised thread of uniform pitch. Shaft 151 is of sufficient torsional strength to accept and transmit rotational finger force applied at the proximal end to the distal end. The ends of helical element 154 are tapered for ease of advancing and retracting the catheter through the abdomen.

Figure 19:
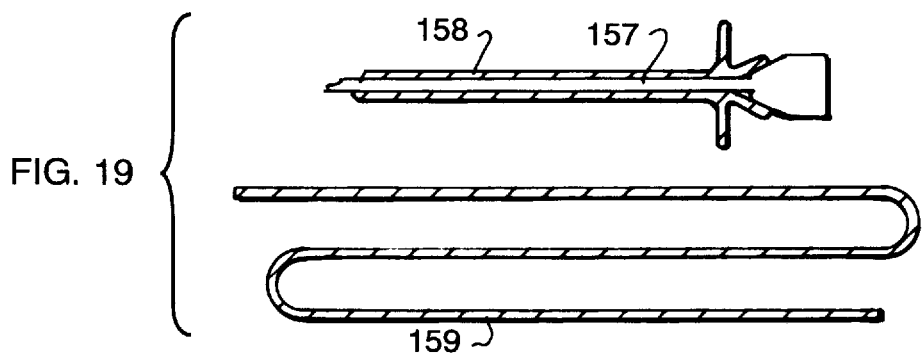
FIG. 19 is a diagrammatic view of a trocar, cannula and guide wire, used to install the suprapubic catheter of FIG. 17.

Referring to FIG. 19, a method by which suprapubic catheter 150 of FIG. 17 is applied is conventional to the extent that trocar 157 and cannula 158 are used with ultrasound or fluoroscopy to create the path through abdomen wall 160 into the bladder organ 161, the trocar is removed, temporary guide wire 159 is then installed through the cannula, and the cannula is then removed. This leaves guidewire 159 as a connecting path extending from outside the body, through the abdominal wall 160, into the bladder organ 161.

Suprapubic catheter 150 is then threaded onto the proximal end of the guide wire, and rotatingly advanced in the same manner as other devices of the invention, through the abdomen towards the bladder organ 161 until external helical element 154 penetrates the organ wall about one full turn. Guide wire 159 is then withdrawn and the distal end of catheter 150 is secured in a non-rotatable fashion to the abdomen wall 160 of the subject using conventional adhesive means, thereby locking the proximal end of the catheter in position in the wall of organ 161.

Referring to FIG. 18, radiopaque markers 155 embedded at points displaced on helical element 154 provide the capability for external detection and monitoring through fluoroscopy or other means of rotational orientation and movement of the distal end of the catheter.

In summary, the method and apparatus of the disclosed screw-based system for emplacement of catheters, stents, occluders and dilators, is a radical departure from thousands of years of prior art of push-in catheters and offers significant advantages in ease of application, safety and wearing comfort over the devices of the known art. It will enhance the convenience, comfort and control of patients, particularly self-administering patients, enabling a broader range of self-administering users to enjoy greater freedom and mobility, and reducing the incidence of injury and infection relating to the shortcomings of the prior art. It is further adaptable to other genito-urinary and gastro-intestinal body passages with similar characteristics.

The objects and advantages of the invention may be further realized and attained by means of the instrumentalities and combinations particularly pointed out in the appended claims. Accordingly, the drawings and description are to be regarded as illustrative in nature, and not as restrictive.

I claim:

1. A medical device for opening strictures in mammalian gastrointestinal and genitourinary passages, comprising a tube with an external helical thread disposed thereon, said thread having a thread height of at least one fifth (⅕) of the outside diameter of said tube and a thread pitch not greater than the circumference of the helix formed by said thread.

2. The medical device of claim 1, further comprising means for determining the position of said device.

3. The medical device of claim 2, said means for determining the position of said device comprising at least one radiopaque marker.

4. The medical device of claim 1, further comprising means for controlling fluid flow through said device.

5. The medical device of claim 1, said device further comprising a fitment secured within said tube and a stylet with a tip, said fitment and said tip configured for axial engagement of said tip into said fitment in a non-rotational manner.

6. The medical device of claim 5, further comprising means for controlling fluid flow through said device.

7. The medical device of claim 1, further comprising sidewall reinforcement.

8. The device of claim 1, wherein said device is constructed of a bioabsorbable or other medically implantable material.

9. A system for implanting a medical device for opening strictures in mammalian gastrointestinal and genitourinary passages, comprising a device follower and a medical device, said device follower comprising an elongate member with an external helical thread disposed thereon, said thread having a thread height of at least one fifth (⅕) of the outside diameter of said member and a thread pitch not greater than the circumference of the helix formed by said thread, said medical device comprising a tube with an external helical thread disposed thereon, said thread having a thread height of at least one fifth (⅕) of the outside diameter of said tube and a thread pitch not greater than the circumference of the helix formed by said thread, one end of said tube configured for self-centering alignment with the proximal end of said device follower.

10. The system for implanting a medical device of claim 9, wherein said elongate member has a lumen sized to accept the ready insertion of a stylet.

11. A method for using the system of claim 9 for implanting a medical device for opening strictures in a mammalian gastrointestinal or genitourinary passage comprising in any order the steps of:

introducing the distal tip of said medical device into an opening of said passage, rotating and advancing said medical device substantially its full length into said passage, aligning and engaging said distal end of said device follower with said proximal end of said stent, rotating and advancing said device follower until said threads of said device follower are engaged in said passage, and rotating said device follower thereby advancing said medical device into place in said passageway.

12. A method for extracting the medical device of claim 10, utilizing said medical device and said device follower in combination with a stylet, wherein said medical device has a fitment secured within said tube, said stylet has a distal end tip, said fitment and said tip are configured for axial engagement of said tip into said fitment in a non-rotational manner, comprising the steps of:

introducing said distal end of said device follower into a opening of said passage, rotating and advancing said device follower until said threads of said device follower are engaged in said passage, rotating said device follower, thereby advancing said device follower into said passage until said distal end of said device follower contacts said proximal end of said medical device, introducing and advancing said stylet through said lumen in said device follower until said tip engages with said fitment of said medical device, counter-rotating said stylet thereby withdrawing said device follower and said medical device from said passage.

* * * * *